US007892249B2

(12) United States Patent
Davison et al.

(10) Patent No.: US 7,892,249 B2
(45) Date of Patent: *Feb. 22, 2011

(54) CANNULA FOR RECEIVING SURGICAL INSTRUMENTS

(75) Inventors: Thomas W. Davison, Franklin, MA (US); Timothy E. Taylor, Hoover, AL (US); Adam Sher, Franklin, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 1330 days.

This patent is subject to a terminal disclaimer.

(21) Appl. No.: 11/417,646

(22) Filed: May 3, 2006

(65) Prior Publication Data

US 2006/0276821 A1 Dec. 7, 2006

Related U.S. Application Data

(63) Continuation of application No. 10/440,231, filed on May 16, 2003, now Pat. No. 7,223,278, which is a continuation of application No. 09/772,605, filed on Jan. 30, 2001, now Pat. No. 6,800,084, which is a continuation-in-part of application No. 09/137,335, filed on Aug. 20, 1998, now Pat. No. 6,187,000.

(51) Int. Cl.
*A61B 17/00* (2006.01)

(52) U.S. Cl. ...................................... 606/190; 600/184

(58) Field of Classification Search ................. 600/201, 600/210, 211, 214, 215, 227, 234; 604/164.01, 604/164.11, 264; 606/86 A, 90, 190
See application file for complete search history.

(56) References Cited

U.S. PATENT DOCUMENTS 1,170,324 A 2/1916 Pomerene
2,605,582 A 8/1952 Allen (Continued)

FOREIGN PATENT DOCUMENTS

AU 13672/95 9/1995

(Continued)

OTHER PUBLICATIONS

Caspar, Wolfhard, M.D.; "The Caspar Microsurgical Discectomy and Comparison with a Conventional Standard Lumbar Disc Procedure" *Neurosurgery*, vol. 28, No. 1; pp. 78-87, Jan. 1991.

(Continued)

*Primary Examiner*—Anhtuan T Nguyen
*Assistant Examiner*—Jonathan W Miles
(74) *Attorney, Agent, or Firm*—Seager, Tufte & Wickhem, LLC

(57) ABSTRACT

A cannula (10) receives surgical instruments (120) for performing a surgical procedure on a body (130). The cannula (10) comprises a tube structure (12) defining a passage (16) through which the surgical instruments (120) are inserted into the body (130). The tube structure (12) has a proximal end (20) and a distal end (62). The tube structure (12) includes an expandable portion (40) for enabling an increase in the cross-sectional area of the passage (16) at the distal end (62). The expandable portion (40) of the tube structure (12), when expanded, has a conical configuration.

20 Claims, 2 Drawing Sheets

U.S. PATENT DOCUMENTS 3,044,461 A 7/1962 Murdock
3,503,398 A 3/1970 Fogarty et al.
3,789,852 A 2/1974 Kim et al.
3,841,317 A 10/1974 Awais
4,449,532 A 5/1984 Storz
4,451,256 A 5/1984 Weikl et al.
4,545,374 A 10/1985 Jacobson
4,573,448 A 3/1986 Kambin
4,601,713 A 7/1986 Fuqua
4,611,594 A 9/1986 Grayhack et al.
4,617,929 A 10/1986 Gill
4,716,901 A 1/1988 Jackson et al.
4,817,587 A 4/1989 Janese
4,819,620 A 4/1989 Okutsu
4,863,133 A 9/1989 Bonnell
4,899,729 A 2/1990 Gill et al.
4,921,478 A 5/1990 Solano et al.
4,984,564 A 1/1991 Yuen
5,025,778 A 6/1991 Silverstein et al.
5,131,382 A 7/1992 Meyer
5,139,499 A 8/1992 Small et al.
5,139,511 A 8/1992 Gill et al.
5,163,949 A 11/1992 Bonutti
5,171,279 A 12/1992 Mathews
5,190,561 A 3/1993 Graber
5,195,541 A 3/1993 Obenchain
5,196,023 A 3/1993 Martin
5,197,971 A 3/1993 Bonutti
5,224,680 A 7/1993 Greenstein et al.
5,232,443 A 8/1993 Leach
5,279,564 A 1/1994 Taylor
5,287,845 A 2/1994 Faul et al.
5,295,994 A 3/1994 Bonutti
5,312,417 A 5/1994 Wilk
5,313,962 A 5/1994 Obenchain
5,345,927 A 9/1994 Bonutti
5,346,504 A 9/1994 Ortiz et al.
5,354,302 A 10/1994 Ko
5,370,647 A 12/1994 Graber et al.
5,370,659 A 12/1994 Sakashita
5,395,317 A 3/1995 Kambin
5,417,203 A 5/1995 Tovey et al.
5,439,464 A 8/1995 Shapiro
5,443,479 A 8/1995 Bressi, Jr.
5,454,365 A 10/1995 Bonutti
5,472,426 A 12/1995 Bonati et al.
5,484,437 A 1/1996 Michelson
5,489,307 A 2/1996 Kuslich et al.
5,490,819 A 2/1996 Nicholas et al.
5,503,617 A 4/1996 Jako
5,520,607 A 5/1996 Frassica et al.
5,529,571 A 6/1996 Daniel
5,556,376 A 9/1996 Yoon
5,571,072 A 11/1996 Kronner
5,575,754 A 11/1996 Konomura
5,601,590 A 2/1997 Bonutti et al.
5,601,690 A 2/1997 Gauld et al.
5,643,282 A 7/1997 Kieturakis
5,649,902 A 7/1997 Yoon
5,667,520 A 9/1997 Bonutti
5,690,606 A 11/1997 Slotman
5,707,359 A 1/1998 Bufalini
5,762,629 A 6/1998 Kambin
5,782,919 A 7/1998 Zdeblick et al.
5,792,044 A 8/1998 Foley et al.
5,795,289 A 8/1998 Wyttenbach
5,813,978 A 9/1998 Jako
5,817,062 A 10/1998 Flom et al.
5,827,319 A 10/1998 Carlson et al.
5,851,214 A 12/1998 Larsen et al.
5,865,802 A 2/1999 Yoon et al.
5,902,231 A 5/1999 Foley et al.
5,954,635 A 9/1999 Foley et al.
5,961,499 A 10/1999 Bonutti et al.
5,976,161 A 11/1999 Kirsch et al.
5,997,508 A 12/1999 Lunn et al.
6,036,638 A 3/2000 Nwawka
6,120,437 A 9/2000 Yoon et al.
6,126,671 A 10/2000 Richards et al.
6,152,871 A 11/2000 Foley et al.
6,162,236 A 12/2000 Osada
6,171,299 B1 1/2001 Bonutti
6,175,758 B1 1/2001 Kambin
6,187,000 B1 2/2001 Davison et al.
6,254,628 B1 7/2001 Wallace et al.
6,306,170 B2 10/2001 Ray
6,312,443 B1 11/2001 Stone
6,338,730 B1 1/2002 Bonutti et al.
6,358,266 B1 3/2002 Bonutti
6,361,488 B1 3/2002 Davison et al.
6,371,968 B1 4/2002 Kogasaka
6,383,195 B1 5/2002 Richard
6,432,048 B1 8/2002 Francois
6,494,893 B2 12/2002 Dubrul et al.
6,497,654 B1 12/2002 Leonard et al.
6,524,320 B2 2/2003 DiPoto
6,530,880 B2 3/2003 Pagliuca
6,530,926 B1 3/2003 Davison
6,564,078 B1 5/2003 Marino et al.
6,589,225 B2 7/2003 Orth et al.
6,620,129 B2 9/2003 Stecker et al.
6,648,888 B1 11/2003 Shluzas
6,652,553 B2 11/2003 Davison et al.
6,800,084 B2 10/2004 Davison et al.
6,811,558 B2 11/2004 Davison et al.
6,821,243 B2 11/2004 Pagliuca et al.
6,837,889 B2 1/2005 Shluzas
6,837,891 B2 1/2005 Davison et al.
6,916,330 B2 7/2005 Simonson
7,001,397 B2 2/2006 Davison
7,004,947 B2 2/2006 Shluzas et al.
7,008,431 B2 3/2006 Simonson
7,033,369 B2 4/2006 Davison et al.
7,056,321 B2 6/2006 Pagliuca et al.
7,066,937 B2 6/2006 Shluzas
7,074,226 B2 7/2006 Roehm, III et al.
7,108,705 B2 9/2006 Davison et al.
7,144,393 B2 12/2006 DiPoto et al.
7,223,278 B2 * 5/2007 Davison et al. ............ 606/198
2003/0014068 A1 1/2003 Bonutti et al.
2003/0139648 A1 7/2003 Foley et al.
2003/0191371 A1 10/2003 Smith et al.
2003/0195405 A1 10/2003 Marino et al.
2003/0195550 A1 10/2003 Davison et al.
2003/0195551 A1 10/2003 Davison et al.
2003/0199871 A1 10/2003 Foley et al.
2004/0078051 A1 4/2004 Davison et al.
2004/0082960 A1 4/2004 Davison
2004/0097907 A1 5/2004 DiPoto
2004/0098012 A1 5/2004 Davison et al.
2004/0116954 A1 6/2004 Pagliuca et al.
2004/0133201 A1 7/2004 Shluzas et al.
2004/0236317 A1 11/2004 Davison et al.
2005/0021030 A1 1/2005 Pagliuca et al.
2005/0033297 A1 2/2005 Davison
2005/0043754 A1 2/2005 Davison et al.
2005/0075540 A1 4/2005 Shluzas et al.
2005/0113833 A1 5/2005 Davison
2006/0089662 A1 4/2006 Davison et al.
2006/0264999 A1 11/2006 Davison et al.
2006/0276822 A1 12/2006 Davison et al.

2006/0293678 A1 12/2006 Davison et al.

FOREIGN PATENT DOCUMENTS

| | | | |
|---|---|---|---|
| EP | 0 528 562 | A2 | 2/1993 |
| EP | 0 807 415 | A2 | 11/1997 |
| EP | 0 807 415 | A3 | 8/1998 |
| EP | 0 980 677 | A1 | 2/2000 |
| EP | 1 251 767 | A2 | 10/2002 |
| EP | 1 305 077 | A1 | 5/2003 |
| FR | 2 701 379 | A1 | 8/1994 |
| JP | 2000-83960 | A2 | 3/2000 |
| JP | 2001-149376 | A2 | 6/2001 |
| WO | WO 92/21292 | A2 | 12/1992 |
| WO | WO 93/14801 | A1 | 8/1993 |
| WO | WO 94/03114 | A1 | 2/1994 |
| WO | WO 95/10218 | A1 | 4/1995 |
| WO | WO 95/22285 | A1 | 8/1995 |
| WO | WO 95/32663 | A1 | 12/1995 |
| WO | WO 01/54560 | A2 | 8/2001 |
| WO | WO 01/54560 | A3 | 8/2001 |
| WO | WO 02/09801 | A1 | 2/2002 |
| WO | WO 02/078767 | A2 | 10/2002 |
| WO | WO 03/007783 | A2 | 1/2003 |

OTHER PUBLICATIONS

Ditsworth, David A., M.D.; "Endoscopic Transforaminal Lumbar Discectomy and Reconfiguration: A Posterolateral Approach into the Spinal Canal", *Surgery & Neurology*, Chapter 49; pp. 588-598.; 1998.

Endius Marketing Bulletin for the *Atavi Atraumatic Spine Fusion System* entitled, "How do I decompress using Atavi System?"; 2002.

Endius Marketing Bulletin for the *Atavi Atraumatic Spine Fusion System* entitled, "Minimally Invasive Update on Danek"; 2002.

Foley, Kevin T., M.D. et al.; "Percutaneous Pedicle Screw Fixation of the Lumbar Spine"; *Neurosurgery Focus*, No. 10; pp. 1-8; Apr. 2001.

Guiot, Bernard H., M.S. et al.; "A Minimally Invasive Technique for Decompression of the Lumbar Spine", *SPINE*, vol. 27, No. 4; pp. 432-438; 2002.

Kambin, Parviz, M.D. and Jonathan L. Schaffer, M.D.; "Arthroscopic Fusion of the Lumbosacral Spine"; *Lumbosacral and Spinopelvic Fixation*, Chapter 44; pp. 565-577; 1996.

Kambin, Parviz, M.D.; "Arthroscopic Lumbar interbody Fusion"; Chapter 77; pp. 1055-1066, date unknown.

Kambin, Parviz, M.D.; "Arthroscopic Lumbar Intervertebral Fusion", *The Adult Spine: Principles and Practice*, Chapter 95; pp. 2037-2046; 1997.

Kambin, Parviz; M.D.; "Arthroscopic Microdiskectomty"; *Mount Sinai Journal of Medicine*; vol. 3; pp. 159-164; 1991.

Kambin, Parviz, M.D.; "Arthroscopic Techniques for Spinal Surgery", *Operative Arthroscopy*, Second Edition; Chapter 89; pp. 1215-1225; 1996.

Kambin, Parviz, "Diagnostic and Therapeutic Spinal Arthroscopy," *Neurosurgery Clinics of North America*, 7(1):65-76, 1996.

Kambin, Parviz, M.D.; "Posterolateral Percutaneous Lumbar Interbody Fusion"; Chapter 9; pp. 117-121, date unknown.

Kambin, Parviz, "The Role of Minimally Invasive Spine Surgery," *Advances in Operative Orthopaedics*, 3:147-171, 1995.

Medtronic Sofamor Danek, "METRx Microdiscectomy Surgical Technique, 2001 as described by Donald L. Hilton, Jr., M.D., F.A.C. S. and Sylvain Palmer, M.D., F.A.C.S."; date unknown.

Medtronic Sofamor Danek; "Minimal Access Spinal Technologies"; *Orthopedics Today*; pp. 1-20; 2002.

Medtronic Sofamor Danek promotional material for the *METRx MicroEndoscopic Discectomy System* entitled, "An Evolution in Minimally Invasive Spine Surgery"; 1999.

Medtronic Sofamor Danek promotional material for the *METRx MicroDisoectomy System* entitled, "The Next Step in Minimally Invasive Discectomy Utilizing the Operating Microscope"; 2000.

Sofamor Danek USA; A manual entitled MED™ MicroEndoscopic Discectomy System by Sofamor Danek USA; pp. 1-33; 1996.

Stauber, Martin H., M.D. et al., "Pedicle Screw Placement with Intraosseous Endoscopy", *SPINE*, vol. 19, No. 1; pp. 57-61; 1994.

Kambin, "Arthroscopic Microdiscectomy," The Adult Spine: Principles and Practice, 94: 2023-2036, 1997.

Kambin, "The Role of Minimally Invasive Surgery in Spinal Disorders," Advances in Operative Orthopaedics, vol. 3: 147-171, 1995.

* cited by examiner 114
112
110
118
106
100
102
116
104
10
66
28
26
24
16
D1
22
80
92
90
74
20
30
14
12
60

62
72
40
12
42
70

22
10
20
12
60
24
72
40
70
62
16
14
66
74
D2

CANNULA FOR RECEIVING SURGICAL INSTRUMENTS

PRIORITY INFORMATION

This application is a continuation of Ser. No. 10/440,231, filed May 16, 2003, now U.S. Pat. No. 7,223,278 which is a continuation of U.S. application Ser. No. 09/772,605, filed Jan. 30, 2001, now U.S. Pat. No. 6,800,084, which is a continuation-in-part of U.S. application Ser. No. 09/137,335, filed Aug. 20, 1998, now U.S. Pat. No. 6,187,000.

TECHNICAL FIELD

The present invention is directed to a cannula for receiving surgical instruments for performing a surgical procedure on a body.

BACKGROUND OF THE INVENTION

Endoscopic surgical techniques allow a surgical procedure to be performed on a patient's body through a relatively small incision in the body and with a limited amount of body tissue disruption. Endoscopic surgery typically utilizes a tubular structure known as a cannula which is inserted into a small incision in the body. The cannula holds the incision open and serves as a conduit extending between the exterior of the body and the local area inside the body where the surgery is to be performed.

Due to the relatively small size of the passage into the body which is defined by the cannula, certain surgical procedures, such as posterior disectomies and procedures using steerable surgical instruments, have been difficult to perform using endoscopic techniques.

SUMMARY OF THE INVENTION

The present invention is a cannula for receiving surgical instruments for performing a surgical procedure on a body. The cannula comprises a tube structure defining a passage through which the surgical instruments are inserted into the body. The tube structure has a proximal end and a distal end. The tube structure includes an expandable portion for enabling an increase in the cross-sectional area of the passage at least at the distal end.

The expandable portion of the tube structure, when expanded, has a conical configuration. The expandable portion of the tube structure includes an arcuate slot and a guide pin disposed in the arcuate slot. The guide pin is movable from a terminal end of the slot to a second terminal end of the slot to enable the cross-sectional area of the passage at the distal end to increase.

The tube structure includes first and second tubular portions attached to one another. The second tubular portion comprises the expandable portion. The first tubular portion comprises a length of stainless steel tubing and the second tubular portion comprises an arcuate segment of stainless steel sheet stock rolled into a tubular shape.

BRIEF DESCRIPTION OF THE DRAWINGS

The foregoing and other features of the present invention will becomes apparent to one skilled in the art to which the present invention relates upon consideration of the following description of the invention with reference to the accompanying drawings, wherein.

DETAILED DESCRIPTION OF THE PREFERRED EMBODIMENT

The present invention is directed to a cannula for receiving surgical instruments for performing a surgical procedure on the body of a patient. The present invention is applicable to a variety of surgical procedures in which endoscopic surgical techniques are used.

Figure 1:
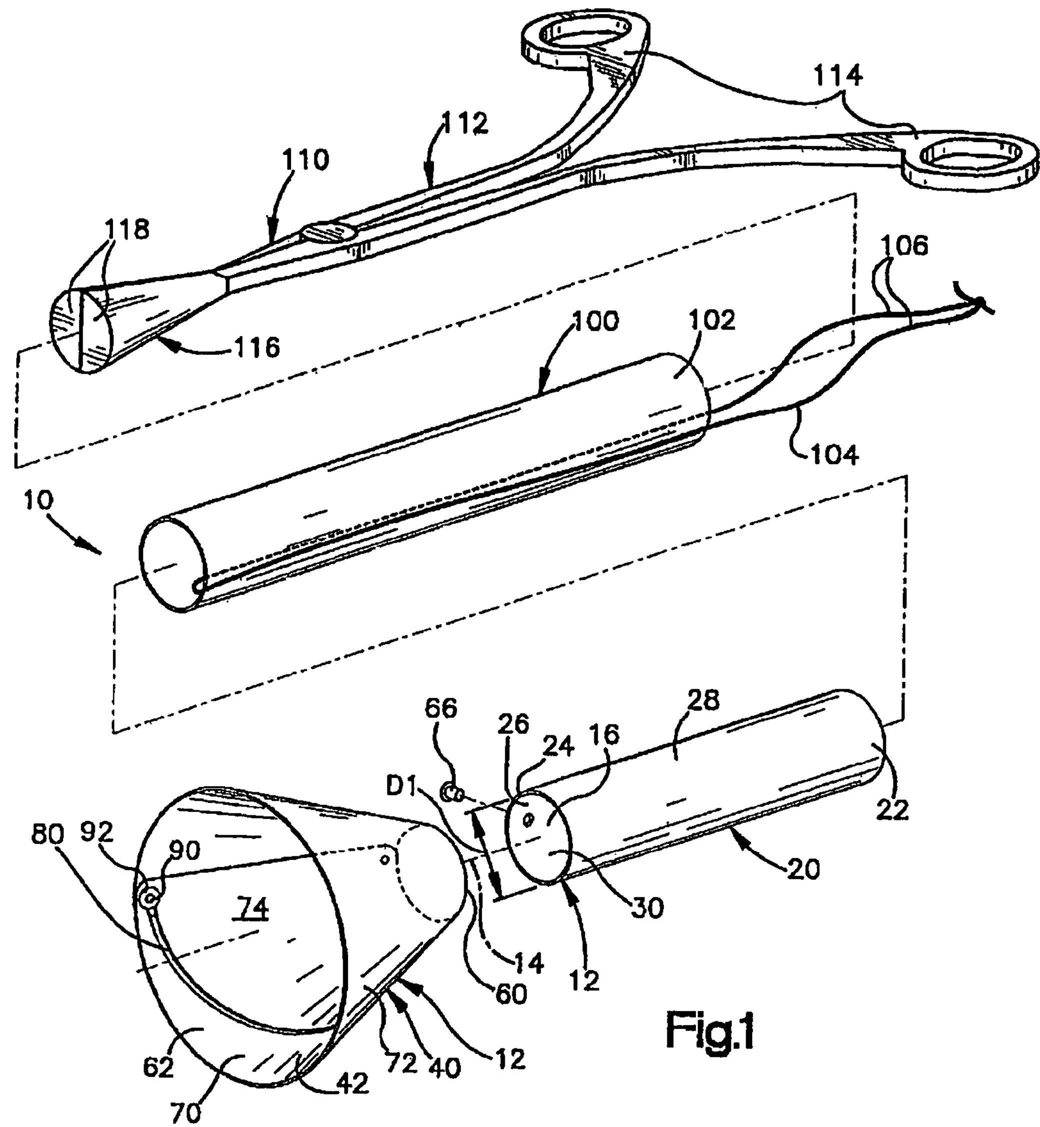
FIG. 1 is an exploded perspective view of a surgical cannula constructed in accordance with the present invention, the cannula being shown in an expanded condition.

FIG. 1 illustrates a cannula 10 constructed according to the present invention. The cannula 10 is a tubular structure 12 centered on an axis 14. The tubular structure 12 defines a passage 16 through the cannula 10. Surgical instruments are inserted into the body during endoscopic surgery through the passage 16.

The tubular structure 12 comprises a first tubular portion 20 and a second tubular portion 40 attached to the first tubular portion. The first tubular portion 20 is preferably made of a length of stainless steel tubing, but could alternatively be made of another suitable material. The first tubular portion 20 has a proximal end 22 and a distal end 24. Parallel cylindrical inner and outer surfaces 26 and 28, respectively, extend between the ends 22, 24 of the first tubular portion 20. The inner surface 26 defines a first passage portion 30 of the passage 16 through the cannula 10. The first passage portion 30 has a diameter D1 which is preferably in the range from 10 mm to 20 mm.

The second tubular portion 40 of the tubular structure 12 is attached to the distal end 24 of the first tubular portion 20. The second tubular portion is preferably made from stainless steel, but could alternatively be made from another suitable material.

Figure 4:
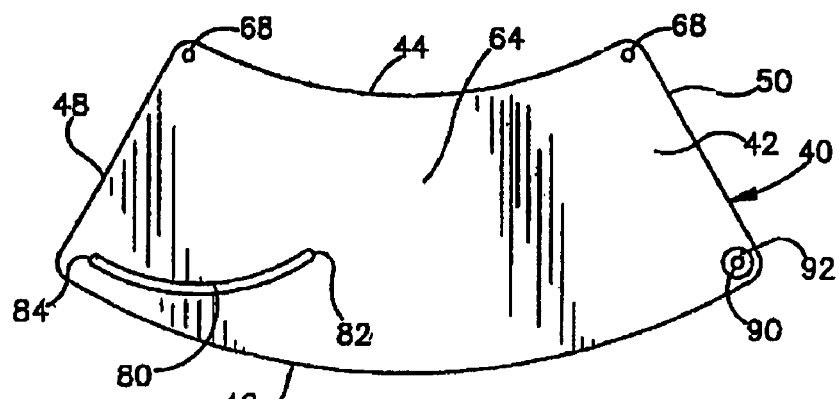
FIG. 4 is a roll out view of a part of the cannula of FIG. 1.

As best seen in the rollout view of FIG. 4, the second tubular portion 40 comprises an arcuate segment 42 of sheet stock. The arcuate segment 42 includes first and second arcuate edges 44 and 46, respectively, and first and second planar edges 48 and 50, respectively. The first and second planar edges 48 and 50 are rolled in an overlapping manner to form the tubular configuration of the second tubular portion 40.

When the second tubular portion 40 has been rolled into its tubular configuration, the first and second arcuate edges 44 and 46 define oppositely disposed first and second ends 60 and 62 (FIGS. 1 and 2), respectively, of the second tubular portion. The first and second ends 60 and 62 are connected by a central portion 64. The first end 60 of the second tubular portion 40 is attached to the distal end 24 of the first tubular portion 20 by a single fastener, such as a rivet 66. The rivet 66 extends through two aligned apertures 68 (FIG. 4) at the first end 60 of the second tubular portion 40. The first end 60 of the second tubular portion 40 is pivotable about the rivet 66.

The second tubular portion 40 includes parallel inner and outer surfaces 70 and 72 (FIGS. 1 and 2), respectively, extending between the first and second ends 60 and 62. The inner surface 70 defines a second passage portion 74 of the passage 16 through the cannula 10 which extends as a continuation of the first passage portion 30 in the first tubular portion 20.

An arcuate slot 80 is formed in the second tubular portion 40 and extends between the inner and outer surfaces 70 and 72 of the second tubular portion. The arcuate slot 80 extends along a curvilinear path in the central portion 64 of the second tubular portion 40 toward the second end 60 of the second tubular portion. The arcuate slot 80 has a first terminal end 82 located in the central portion 64 of the second tubular portion 40. A second terminal end 84 of the arcuate slot 80 is located adjacent the intersection of the second arcuate edge 46 and the first planar edge 48 of the arcuate segment 42.

A guide pin 90 is attached to the inner surface 70 of the second tubular portion 40 adjacent the intersection of the second arcuate edge 46 and the second planar edge 50. In the tubular configuration of the second tubular portion 40, the guide pin 90 is located in the arcuate slot 80 and is movable along the curvilinear path of the arcuate slot. A washer 92 is secured an inner end of the guide pin 90 to retain the guide pin in the arcuate slot 80.

Figure 2:
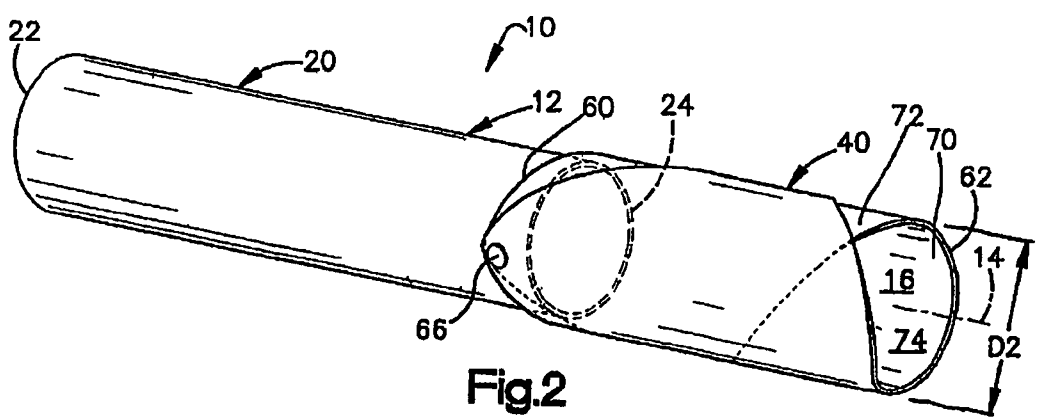
FIG. 2 is a perspective view of the cannula of FIG. 1 with parts removed for clarity, the cannula being shown in a contracted condition.
Figure 3:
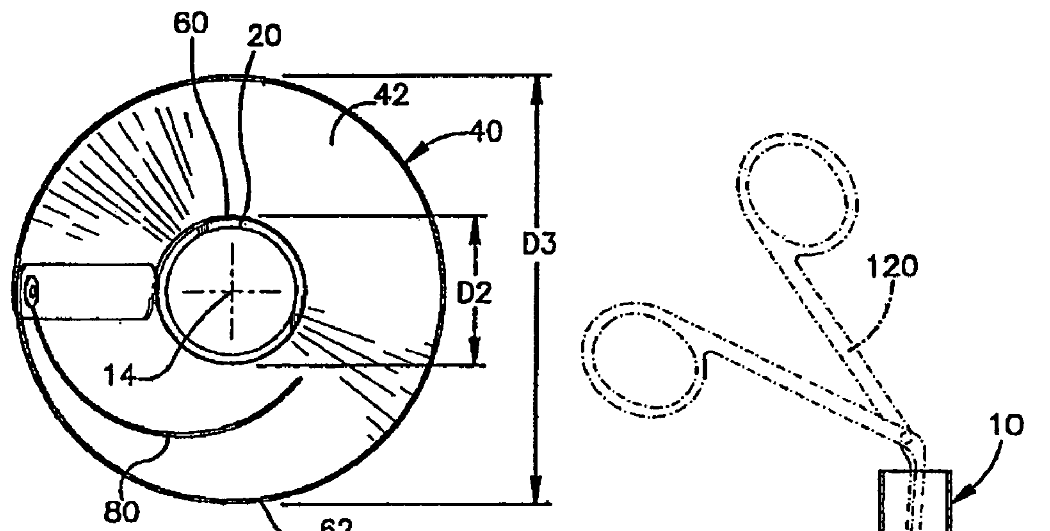
FIG. 3 is a schematic end view showing the cannula of FIG. 1 in the expanded position.

The second tubular portion 40 of the tubular structure 12 is expandable from a contracted condition shown in FIG. 2 to an expanded condition shown in FIG. 1. In the contracted condition, the guide pin 90 is located in the first terminal end 82 of the arcuate slot 80 in the second tubular portion 40 and the second passage portion 74 defined by the second tubular portion is cylindrical in shape. The second passage 74 has a generally constant diameter D2 (FIGS. 2 and 3) which is approximately equal to the diameter D1 of the first tubular portion 20. Thus, the cross-sectional area of the second passage portion 74 at the second end 62 of the second tubular portion 40, which is function of the diameter D2, is approximately the same as the cross-sectional area at the first end 60 of the second tubular portion and is approximately the same as the cross-sectional area of the first passage portion 30 in the first tubular portion 20.

In the expanded condition, the guide pin 90 is located in the second terminal end 84 of the arcuate slot 80 in the second tubular portion 40 and the second tubular portion has a conical configuration. At the second end 62 of the second tubular portion 40, the second passage portion 74 has a diameter D3 (FIG. 3) which is larger then the diameter D2 of the second passage portion at the first end 60. Preferably, the diameter D3 of the second passage portion 74 at the second end 62 of the second tubular portion is 40% to 80% greater than the diameter D1 of the second passage portion at the first end 60. Thus, in the expanded condition, the cross-sectional area of the second passage portion 74 at the second end 62 of the second tubular portion 40, which is function of the diameter D3, is 40% to 80% greater than the cross-sectional area of the second passage portion at the first end 60 of the second tubular portion.

The cannula 10 includes an outer layer 100 (FIG. 1) for maintaining the second tubular portion 40 of the cannula in the contracted condition. It is contemplated that other suitable means for maintaining the second tubular portion 40 in the contracted condition could be employed. In accordance with a preferred embodiment of the present invention, the outer layer 100 comprises a section of plastic tubing 102 which is heat shrunk over both the first and second tubular portions 20 and 40 to hold the second tubular portion in the contracted condition.

In addition, a loop of nylon string 104 for tearing the heat shrunk tubing 102 is wrapped around the heat shrunk tubing so that it extends both underneath and on top of the tubing. An outer end 106 of the string 104 extends beyond the tubing 102.

The cannula 10 further includes an actuatable device 110 for expanding the second tubular portion 40 from the contracted condition to the expanded condition. In accordance with a preferred embodiment of the present invention, the actuatable device 110 comprises a manually operated expansion tool 112. The expansion tool 112 resembles a common pair of scissors and has a pair of legs 114 pivotally connected to one another. The expansion tool 112 includes a frustoconical end section 116 formed by a pair of frustoconical halves 118. Each of the frustoconical halves 118 extends from a respective one of the legs 114 of the expansion tool 112. It is contemplated that other suitable means for expanding the second tubular portion 40 toward the expanded condition could be employed, such as an inflatable balloon (not shown).

During an endoscopic surgical procedure, the cannula 10 is inserted into the body of a patient in the contracted condition. The outer end 106 of the string 104 is then manually pulled on by the surgeon. Pulling on the string 104 tears the heat shrunk tubing 102 which is then removed from the cannula 10 by the surgeon. With the heat shrink tubing 102 removed, the second tubular portion 40 of the cannula 10 is thereby released for expansion toward the expanded condition.

Figure 5:
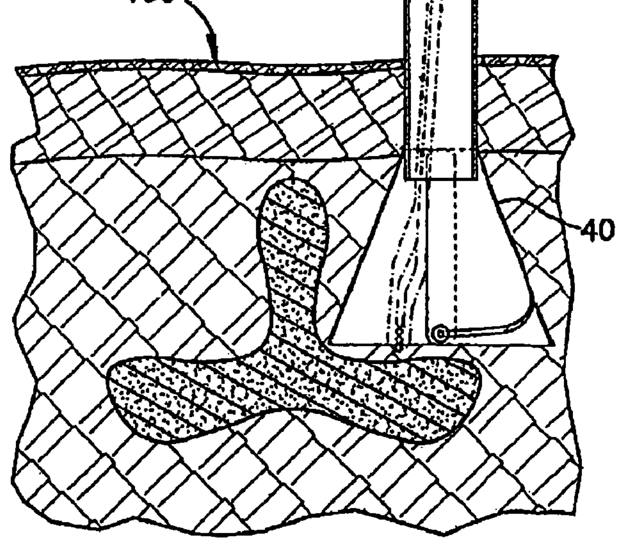
FIG. 5 is a schematic sectional view of the cannula of FIG. 1 during a surgical procedure.

Next, the expansion tool 112 is inserted into the passage 16 in the cannula 10 until the frustoconical end section 114 is located at the second end 62 of the second tubular portion 40. The legs 114 of the expansion tool 112 are manually separated, causing the frustoconical halves 118 to separate also. As the halves 118 separate, a radially outward directed force is exerted on the inner surface 70 of the second tubular portion 40 by the halves 118, causing the second tubular portion to expand toward the expanded condition. Under the force of the expanding expansion tool 112, the guide pin 90 slides from the first terminal end 82 of the arcuate slot 80 to the second terminal end 84 of the arcuate slot to permit the expansion of the second tubular portion 40. The expansion tool 112 can be rotated about the axis 14 to ensure that the second tubular portion 40 of the cannula 10 is completely expanded to the expanded condition. The expansion tool 112 is then collapsed and removed so that one or more surgical instruments (indicated schematically at 120 in FIG. 5) can be received through the cannula 10 and inserted into a patient's body 130.

The expandable second tubular portion 40 of the cannula 10 provides a significantly larger working area for the surgeon inside the body 130 within the confines of the cannula. As a result, the simultaneous use of a number of endoscopic surgical instruments, including but not limited to steerable instruments, shavers, dissectors, scissors, forceps, retractors, dilators, and video cameras, is made possible by the expandable cannula 10.

It is contemplated that the cannula 10 described herein could be the centerpiece of a endoscopic surgical kit which would include an assortment of surgical instruments designed and/or selected for use with the cannula.

From the above description of the invention, those skilled in the art will perceive improvements, changes and modifications. Such improvements, changes and modifications within the skill of the art are intended to be covered by the appended claims.

What is claimed is:

1. A device for providing access to a spinal location within a patient, said device comprising:

an elongate body having a proximal portion pivotally connected to a distal portion and defining a length therebetween such that when the distal portion is positioned inside the patient adjacent the spinal location, at least part of the proximal portion extends outside the patient, wherein the distal portion includes a slot and a guide member disposed in the slot and moveable within the slot, wherein movement of the guide member along the slot results in expansion or contraction of at least part of the distal portion, wherein the guide member is an expansion limiter, preventing the distal portion from expanding beyond a predetermined limit; and an expander comprising a first pivoting member configured to engage a first side of the elongate body and a second pivoting member configured to engage a second side of the elongate body, the second side being opposite the first side, the expander configured to move the guide member along the slot, thereby expanding the elongate body such that a transverse dimension extending between the first and second sides of the elongate body at a first location is greater than a transverse dimension extending between the first and second sides of the elongate body at a second location, wherein the first location is distal to the second location;

wherein the elongate body provides an access path to the spinal location between the first and second sides, the access path sized such that more than one surgical instrument can be advanced simultaneously along the access path between a proximal end and the spinal location.

2. The device of claim 1, wherein the elongate body comprises rigid material extending around substantially the entire perimeter at least at one of said first and said second locations.

3. The device of claim 2, wherein the distal portion of the elongate body has a proximal region connected to the proximal portion, and a distal region configured to be disposed adjacent the spinal location, wherein the slot and guide member are disposed in the distal region of the distal portion.

4. The device of claim 1, wherein the elongate body comprises an inner surface comprising a smooth metal.

5. The device of claim 1, wherein the expander comprises a pair of legs pivotally connected to one another.

6. The device of claim 1, wherein the expander is configured to be inserted into the elongate body such that the first pivoting member can be coupled with the first side of the elongate body and the second pivoting member can be coupled with the second side of the elongate body.

7. The device of claim 1, wherein the elongate body comprises an inner surface, an outer surface, and an area of overlap between the inner and outer surfaces, and wherein actuating the expander reduces the area of overlap.

8. The device of claim 7, wherein the guide member is disposed on the outer surface and the slot extends between the inner and outer surfaces, wherein the slot and guide member are located in the area of overlap.

9. The device of claim 7, wherein the first and second pivoting members each have a distal portion with an outer surface having a geometry that corresponds with a geometry of the inner surface of the elongate body.

10. The device of claim 9, wherein when the distal portions of the first and second pivoting members are adjacent each other, they create a frustoconical configuration.

11. The device of claim 1, wherein the proximal and distal portions are connected at a single pivot point such that they are capable of pivoting relative to each other, and wherein actuating the expander causes the two portions to pivot relative to each other.

12. The device of claim 1, wherein the expander is configured to expand the distal portion of the elongate body without expanding the proximal portion.

13. The device of claim 1, wherein the elongate body is configured such that once expanded, the expanded configuration is maintained when the expander is removed.

14. The device of claim 1, wherein the distal portion of the elongate body comprises an arcuate segment of sheet stock rolled into a tubular shape.

15. A device for providing access to a spinal location within a patient, said device comprising:

an elongate body having a proximal portion pivotally connected to a distal portion and defining a length therebetween when the distal portion is positioned inside the patient adjacent the spinal location, at least part of the proximal portion extends outside the patient, wherein the distal portion includes a slot and a guide member moveable within the slot, wherein the slot is arcuate and extends from a first end disposed adjacent a distal end of the distal portion to a second end disposed proximal of the first end, wherein movement of the guide member from the first end of the slot to the second end of the slot results in expansion of at least part of the distal portion; and an expander configured to be inserted into and removed from the elongate body, the expander comprising a first pivoting member configured to engage a first side of the elongate body and a second pivoting member configured to engage a second side of the elongate body, the second side being opposite the first side, the expander configured to move the guide member from the first end to the second end of the slot, thereby expanding the elongate body such that a transverse dimension extending between the first and second sides of the elongate body at a first location is greater than a transverse dimension extending between the first and second sides of the elongate body at a second location, wherein the first location is distal to the second location;

wherein the elongate body provides an access path to the spinal location between the first and second sides, the access path sized such that more than one surgical instrument can be advanced simultaneously along the access path between a proximal end and the spinal location.

16. The device of claim 15, wherein the elongate body comprises rigid material extending around substantially the entire perimeter at least at one of said first and said second locations.

17. The device of claim 15, wherein the elongate body comprises an inner surface, an outer surface, and an area of overlap between the inner and outer surfaces, and wherein actuating the expander reduces the area of overlap.

18. The device of claim 15, wherein the proximal and distal portions of the elongate member are connected at a single pivot point such that they are capable of pivoting relative to each other, and wherein actuating the expander causes the two portions to pivot relative to each other.

19. The device of claim 15, wherein the elongate body is configured such that once expanded, the expanded configuration is maintained when the expander is removed.

20. The device of claim 15, wherein the distal portion of the elongate body comprises an arcuate segment of sheet stock rolled into a tubular shape.

* * * * *